US005672594A

United States Patent [19]
Weis et al.

[11] Patent Number: 5,672,594
[45] Date of Patent: Sep. 30, 1997

[54] L-ERYTHROSYL NUCLEOSIDES

[75] Inventors: Alexander L. Weis; Tamas Bakos, both of San Antonio, Tex.; Charles T. Goodhue, Rochester, N.Y.

[73] Assignee: Genencor International, Inc., Rochester, N.Y.

[21] Appl. No.: 328,301

[22] Filed: Oct. 24, 1994

[51] Int. Cl.$^6$ .................................................. A61K 31/70
[52] U.S. Cl. ........................... 514/45; 514/46; 514/49; 514/50; 536/27.14; 536/27.21; 536/27.6; 536/27.61; 536/27.62; 536/27.63; 536/27.7; 536/27.8; 536/27.81; 536/28.1; 536/28.5; 536/28.51; 536/28.52; 536/28.53; 536/28.54; 536/28.55
[58] Field of Search .................... 536/1.11, 4.1, 536/17.1, 26.7, 26.8, 28.1, 28.5, 28.53, 28.54, 28.56; 514/45, 46, 49, 50, 47, 48, 51; 544/242, 262

[56] References Cited

U.S. PATENT DOCUMENTS 5,075,446 12/1991 Kim et al. .

FOREIGN PATENT DOCUMENTS 2648239 4/1977 Germany .

OTHER PUBLICATIONS

Ozaki, S. et al. (2986) Chem & Pharma. Bull. 34(1):150–157.
Miwa, M. et al. (1986) Chem. & Pharma. Bull. 34(10):4225–4232.
Phadtare, S. et al. (1989) J. Am. Chem. Soc. 111(15):5925–5931.
Chemical Abstracts (986) No. 226624e 105(25):798.
Lee, C.H. et al. (1990) Heterocycles 31(1):211–214.
Chemical Abstracts (1977)No. 168348q 87(21):609.
Chemical Abstract (1980) No. 168560b 93(17):711.
Chemical Abstracts (1979) No. 175368p 91(21):670.
Chemical Abstracts (1980) No. 59160e 92(7):714.
Chemical Abstracts (1986) No. 60481d 105(7):602.
Chemical Abstracts (1987) No. 115913v 107(13):662.
Chemical Abstracts (1988) No. 132218k 108(15):797.
Noell, C.W. et al., (1968) J. Heterocyclic Chem. 5(1)25–28.

Primary Examiner—James O. Wilson
Attorney, Agent, or Firm—Margaret A. Horn

[57] ABSTRACT

This invention relates to α and β-L-erythrosyl nucleosides of the formula (I), wherein the nucleoside substitution on the erythrosyl carbohydrate molecule comprises a substituted or unsubstituted purine (adenine or guanine) or pyrimidine (cytosine, uracil, thymine and hypoxanthine) base. Also provided are methods to make the α and β-L-erythrosyl nucleosides and methods of using such to treat cancer in a mammal.

11 Claims, No Drawings

L-ERYTHROSYL NUCLEOSIDES

FIELD OF THE INVENTION

This invention relates to L-erythrosyl nucleosides, processes for their preparation, pharmaceutical compositions containing such and methods of using such compounds as anticancer, antiviral, antifungal, antiparasitic and/or antibacterial agents in meals.

BACKGROUND OF THE INVENTION

Perigaud, C., et al., *Nucleosides and Nucleotides*, 11(2-4), 903-945, (1992), provide a useful overview of the current state of the art relating to the use of nucleosides and/or nucleotides as chemotherapeutic agents (including use as anticancer, antiviral and antibacterial agents). As described in this review article, the term "nucleoside(s)" relates to naturally-occurring nucleosides which are distinguished depending on the base, for example, adenine and guanine (A and G, respectively) have a purine base, whereas cytosine, uracil, thymine and hypoxanthine (C, U, T and H, respectively) have a pyrimidine base.

Genù-Dellac, C., et al., *Nucleotides & Nucleosides*, 10(6), 1345-1376, (1991), describe the synthesis of the 2'-deoxy-α-L-erythro-pentofuranosyl analog of naturally-occurring nucleosides and their use as antiviral compounds.

Nagasawa, N. et al., *J. Org. Chem.*, 32, 251-252, (1967), describe the production of certain D-ribopyranosyl nucleosides (particularly 9-(2'-Deoxy-β-D-ribopyranosyl) adenosine. Fucik, V., et al., *Nucleic Acids Research*, Vol. 1, No. 4, (1974), 639-644, describe structural effects of chemical modification upon the affinity of purine nucleosides to cytidine-transport system in *Bacillus subtilis* using a series of modified derivatives including certain ribopyranosyl nucleosides.

As is well known, sugars found in natural nucleic acids are D-ribose and D-deoxyribose in almost all cases. Much research has been done to investigate the chemical and biological activities of the D-isomers of ribonucleotides and ribonucleosides, however, far less work has been done with the L-isomers. This is primarily due to the fact that the synthesis of the L-isomers is much more difficult, often involving the optical resolution of the DL-isomers of nucleosides with the aid of microorganisms and enzymes. (See generally, Asai, M., et al., *Chem. Pharm. Bull.*, 15(12), 1863-1870, (1967).) The known activity of D-nucleoside compounds, and the successful commercialization of several of such D-sugar-nucleoside compounds (See Perigaud, C., et al., supra, for a discussion of D-nucleoside analogs which have gained commercial acceptance) led in-part to the present work relating to the L-isomers of certain nucleoside analogs.

Perhaps the best known commercial nucleobase analog is 5-fluorouracil (5-FU) the structure of which is shown below:

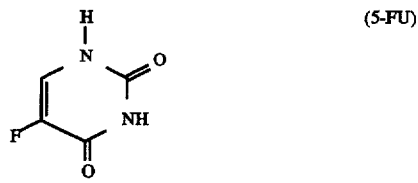

(5-FU)

5-FU is an antimetabolite compound commercially available from Roche and is one of the most commonly used drugs for treating certain types of cancer. The high acceptance of this drug is due in part to its extreme cytotoxic effects. However, this highly toxic compound has a narrow margin of safety and it has many side effects including, for example, nausea, vomiting, diarrhea, leukopenia, thrombocytopenia, alopecia, etc. Additionally, 5-FU is primarily used in an intravenous formulation only. Therefore, there is a need for a nucleoside analog which is perhaps as cytotoxic as 5-FU or which is less cytotoxic but more specific than 5-FU, and which preferably can be administered orally.

5-FU is currently dosed at short intervals due to the damage it does to normal cells. The patient is taken off chemotherapy for a time to allow recovery from the cytotoxic effects of the treatment. It is contemplated that if a drug is developed that is less cytotoxic to healthy cells, it would no longer be necessary to treat the patient in periodic intervals, which may be associated with the development of multiple drug resistance often exhibited in treated cancer cells. Specifically, as a tumor is being killed, the cells that are most resistant to the drug die slower and, therefore, when the treatment is stopped (often because of the toxicity to normal cells) the more resistant tumor cells are left to multiply.

A significant commercial nucleoside analog is azidothymidine (AZT), commercially available as Retrovir from Burroughs Wellcome. AZT, a β-D-deoxy-ribofuranosyl derivative of the formula:

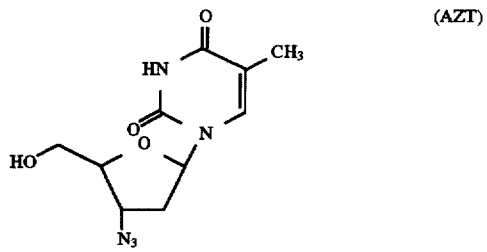

(AZT)

is useful as an antiviral agent, particularly against the virus responsible for the Acquired Immune Deficiency Syndrome (AIDS).

This compound, like 5-FU, is associated with a number of undesirable side effects including hematologic toxicity such as granulocytopenia and/or severe anemia.

Without intending to be limited, applicants believe that the L-nucleoside compounds as claimed in the present invention may be beneficial over compounds such as 5-FU and AZT since it is believed that L-nucleosides (as claimed) exhibit selective permeability to compromised cells. By compromised cells we mean cells such as cancer cells or other infected cells, whether the infection is bacterial, fungal, viral or parasitic. It is believed that the L-nucleosides of the present invention may be transported into or permeate these compromised cells, whereas in normal cells the L-nucleosides would not permeate. (See for example, Lin, T. S., et al., Abstract entitled "Synthesis and Biological Evaluation of 2', 3'-Dideoxy-L-Pymidine Nucleosides as Potential Antiviral Agents Against HIV and HBV", published *J. Med. Chem.*, 37, (1994), p. 798-803; and Spadari, S., et al., *J. Med. Chem.*, 35, (1992), p. 4214-4220). Therefore, to the extent these L-nucleosides are selective for compromised cells, they are less harmful to normal cells than compounds like 5-FU.

In addition to this concept of selective permeability, in viral-infected cells where therapeutic compounds often have an inhibitory mechanism related to the RNA of the cell, it is contemplated that the enzymes of such viral infected cells may be less specific than in a normal cell and, therefore, if one can permeate the cell with an L-nucleoside, a more primitive enzyme (such as an organic phosphorylase, kinase or thymidilate synthase) may recognize the compound in such a way as to cause inhibition.

The present invention relates to a novel group of such L-erythrosyl nucleosides which have interesting activity as anticancer, antiviral, antiparasitic, antifungal and/or antimicrobial agents. These compounds are generally water soluble, which suggests that oral deliver may be achieved. This would be specifically advantageous versus 5-FU and similar anticancer agents. Also, the activity of these compounds may be more selective for compromised cells as compared to normal cells, suggesting that compounds of this invention may cause fewer side effects.

DETAILED DESCRIPTION OF THE INVENTION

There is provided by this invention erythrosyl nucleoside compounds having the formula (I):

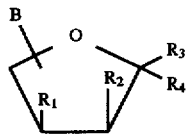

or a pharmaceutically acceptable salt thereof, wherein:

B is a naturally-occurring nucleoside (A, G, C, U, hypoxanthine or T) or a modified nucleobase comprising one or more substitutions selected from the group consisting of H, halogen, C1–C6 alkyl, C2–C6 alkenyl, C1–C6 alkoxy, C3–C6 cycloalkyl C1–C6 alkoxy, C3–C8 cycloalkyloxy, C3–C8 cycloalkylthio, C1–C6 alkylthio, a substituted amino group, an aryl, aralkyl, aryloxy, aralkoxy, arylthio, aralkylthio, a heterocyclic ring and an amino group, provided that when the base is a pyrimidine, the atom at position 4 of the base can be sulfur and further provided that when the base is a purine, the atom at position 6 of the base may be sulfur;

$R_1$ and $R_2$ are independently H, mono- or di-halogen, $OR_5$, or B (wherein $R_5$ is H, $COR_6$, $P(O)_n R_7 R_8$ (wherein $R_6$ is substituted or unsubstituted alkyl of 1–5 carbon atoms or a substituted or unsubstituted aromatic ring structure, $R_7$ and $R_8$ are each H or alkyl of 1–5 carbon atoms and n is 2 or 3)); and $R_3$ and $R_4$ are independently B, H or $OR_9$ (where $R_9$ is H, $COR_{10}$, $P(O)_m R_{11} R_{12}$ (wherein $R_{10}$ is substituted or unsubstituted alkyl of 1–5 carbon atoms or a substituted or unsubstituted aromatic ring structure and $R_{11}$ and $R_{12}$ are each H or alkyl of 1–5 carbon atoms and m is 2 or 3)), provided that: only one of $R_1$–$R_4$ can be B; when $R_4$ is B and B is 5-fluorouracil then $R_1$ and $R_2$ can not both be H; when $R_1$ and $R_2$ are OH, $R_3$ is H, and $R_4$ is B, then B cannot be A; and when $R_1$ and $R_2$ are OH, $R_4$ is H, and $R_3$ is B, then B cannot be A.

Preferred compounds of the present invention include those compounds of formula (I) wherein:

one of $R_3$ or $R_4$ is B and the other is H, such that when $R_3$ is B the series is α and when $R_4$ is B, the series is β;

B is C, T, U, G, A, hypoxanthine, and 5-fluorouracil; and $R_1$–$R_2$ are each OH.

Specifically preferred compounds of the present invention are the following:

β-L-erythrofuranosyl-5-fluorouracil; β-L-erythrofuranosyluracil; β-L-erythrofuranosylcystosine; β-L-erythrofuranosylhypoxanthine; β-L-erythrofuranosylguanine; α-L-erythrofuranosyl-5-fluorouracil; and 3'-azido-2', 3'-dideoxy-β-L-erythrofuranosylthymine or a pharmaceutically acceptable salts thereof.

Also provided by this invention are processes for the preparation of the compounds of formula (I), pharmaceutical compositions containing the compounds of formula (I), and methods of using the compounds of formula (I) for the treatment of cancer in a mammal (particularly a solid tumor cancer), as well as methods of using the compounds of formula (I) as antiviral, antifungal, antiparasitic and/or antibacterial agents in a mammal.

Synthesis

The present invention describes a series of L-erythro nucleosides useful for treating various diseases (including cancer). Compounds of this invention may be orally active based on their water solubility.

Certain compounds of Formula I of the present invention can be made by the general Scheme A. Although the schematic is specific for the production of compound 5 starting from a chloro-benzene diol (protected as an acetonide), it will be readily understood by those skilled in the art that other compounds within the scope of this invention may be made via similar routes using known methods such as those described in *Nucleic Acid Chemistry, Improved and New Synthetic Procedures, Methods and Techniques*, edited by Leroy B. Townsend and R. Stuart Tipson, (1978); and *Chemistry of Nucleosides and Nucleotides*, edited by Leroy B. Townsend, New York, Plenum Press, (1988–1991). Suitable methods for making various substitutions on purine nucleosides are provided in WO090/08147. Suitable methods for making substitutions on pyrimidine nucleosides are provided in WO88/04662. The disclosure of all such applications and references being readily available to those skilled in the art and incorporated herein as background information. Suitable methods for making substitutions within the sugar moiety of the presently claimed compounds are known to those skilled in the art and are described in various publications including: U.S. Pat. No. 4,880,782; WO88/00050; EPO 199451 A2; U.S. Pat. No. 3,817,982; Lange, P., et al., Progress in Antimicrobial and Anticancer Chemotherapy, Proceedings of the 6th International Congress of Chemotherapy, Univ. Park Press, England, 1970, Vol. II, p. 394–397; and Townsend, et al., supra.

SCHEME A

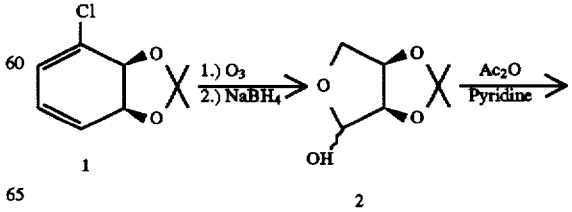

-continued
SCHEME A

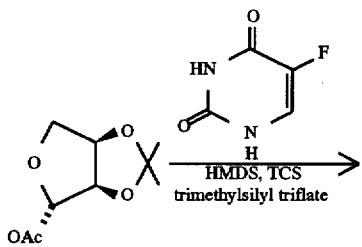

3

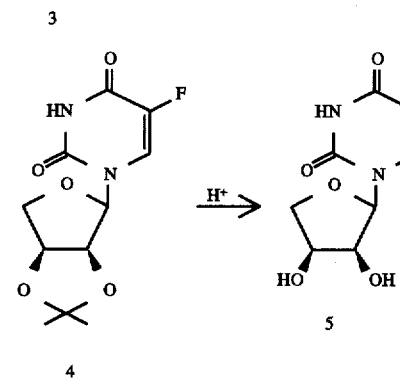

4   5

EXAMPLE 1

α-L-erythrofuranosyl5-fluorouracil (5)

Step A

A solution of (2S,3S)-2,3-O-isopropylidene-1-chlorocyclohexa-4,6-diene 1 (22.2 g) in MeOH—$CH_2Cl_2$ (8:2) was cooled to −78° C. and a stream of $O_3/O_2$ was passed through until the persistence of blue color. Argon was bubbled through the solution to remove the excess ozone. To a stirred solution at −78° C. under Ar atmosphere $NaBH_4$ (4.39 g) was added portionwise. After addition, stirring was continued for 1 hour. The temperature was raised to 0° C. and the solution was stirred for an additional hour. Then 210 ml of saturated ammonium chloride was added. Solvent was removed in vacuo. The semi-solid residue was taken up in EtOAc (150 ml) and filtered. This operation was repeated twice. After evaporation a combined organic extract 18.8 g yellow liquid was obtained. Purification by flash chromatography (petroleum ether-ethyl acetate, 6:4) yielded 8.8 g of 2 as a pale yellow oil. ($R_f$=0.34 PE-EtOAc 50:50).

Step B 2,3-O-isopropylidene-L-erythrose 2 (4 g) was dissolved in pyridine (5 ml) and acetic anhydride (15 ml) at room temperature. After 1 hour TLC showed complete conversion to 3. The reaction mixture with $CH_2Cl_2$ (100 ml) was washed successively with saturated $NaHCO_3$ solution and water. The organic phase was dried over $Na_2SO_4$ and evaporated to dryness to give 3 (5.05 g, 98%) as a yellow oil ($R_f$=0.63, PE-EtOAc 50:50).

Step C

To a solution of 3 (2.5 g) and 5-fluorouracil (1.6 g) in acetonitrile (50 ml) hexamethyldisilazane (2.1 ml) chlorotrimethylsilane (1.3 ml) and trimethylsilyl triflate (3.0 ml) were added. After stirring for 60 hours at room temperature TLC showed the completion of the reaction. Then $CH_2Cl_2$ (100 ml) was added and the mixture extracted with 3×50 ml of saturated $NaHCO_3$ solution. The organic phase was dried over $Na_2SO_4$ and evaporated to give 2.2 g crude material, which was purified to furnish 0.88 g of white crystalline product 4 ($R_f$=0.17, PE-EtOAc 50:50).

Step D

Hydrolysis of 4 in 1N HCl solution gave 5 (0.55 g) as a white crystalline material.

(DMSO-d6)δ3.75 (dd,1H,H-4'a) 3.90 (dd,1H,H-4'b) 4.15 & 4.30 (m,2H,H-2' & 3") 5.40 & 5.55 (br s,2H,2' & 3"-OH) 6.0 (dd,1H,H-1') 11.80 (s,1H,NH)

Utility

In vitro activity against certain human tumor cell lines.

CELL LINES: Eight different established human cell lines CALU (lung), COLO320 (colon), H578St (breast), HT-29 (colon), MCF-7 (breast), OM-1 (colon), SKLU (lung) and SKMES (lung), and two control cell lines (bone marrow and/or fibroblasts) were utilized.

All cell lines were obtained from the Tumor Cloning Laboratory, Institute for Drug Development, Cancer Therapy and Research Center, San Antonio, Tex. All cell lines grew as monolayers in the appropriate culture medium supplemented with heat-inactivated calf serum. All reagents were obtained from Grand Island Biological Co., Grand Island, N.Y.

IN VITRO EXPOSURE OF TUMOR CELLS TO COMPOUNDS: Stock solutions of intravenous (iv) formulations of certain of the compounds of the present invention (as shown in Table I below), as well as intravenous formulations of 5-FU (control) were used. The iv formulations of the compounds of the present invention were prepared with sterile buffered saline and stored at −70° C. until required for testing. The 5-FU control formulation was prepared as suggested in the commercial product literature.

Following trypsinization, tumor cells were suspended in tissue culture medium and exposed to the antitumor agents continuously at three different concentrations: 10, 1 and 0.1 μg/ml.

RADIOMETRIC MEASUREMENT OF GROWTH INHIBITION: Growth inhibition was assessed with the BACTEC System 460 (Johnston Laboratories, Towson, Md.) after addition of the antitumor agent in the respective growth medium containing $^{14}C$-glucose at a final concentration of 2 μCi/ml. (See generally, C. Arteaga, et al., A Radiometric Method for Evaluation of Chemotherapy Sensitivity: Results of Screening a Panel of Human Breast Cancer Cell Lines, Cancer Research, 47, 6248–6253, (1987)).

Two mls of the tumor cell suspension containing radioactive glucose were seeded into sterile, disposable 15 ml vials by injection through self-sealing rubber-aluminum caps. For each cell line, the optimal number of tumor cells needed per vial in order to show significantly measurable growth in this radiometric system varied. The seeded vials were then incubated at 37° C. Measurement of the release of $^{14}CO_2$ resulting from the metabolism of $^{14}C$-glucose were performed on days 6, 9, 12, and 15 in the BACTEC instrument. This instrument flushes the $^{14}CO_2$ containing air out of the vials into an ionization chamber that converts dpm to growth index values. Chemotherapy sensitivity was calculated by comparing the growth index values of drug-treated vials to that observed in control vials. Each data point represents triplicate values.

Results are shown in Table I below.

TABLE I

| COMPOUND | % SURVIVAL BONE MARROW | % SURVIVAL TUMOR | | IC 50 |
|---|---|---|---|---|
| 5-FU | 38.6 | CALU | 9.9 | <0.6 |
| | | COLO320 | 1.0 | <0.6 |
| | | HS578T | 12.5 | >0.6 |
| | | HT29 | 5.7 | 0.613 |
| | | MCF-7 | 4.2 | <0.6 |
| | | OM-1 | 20.1 | 1.47 |
| | | SKLU | 24.7 | 1.049 |
| | | SKMES | 29.1 | <0.6 |
| α-L-erythro furanosyl-5-fluorouracil | 104 | CALU | 85.3 | >10 |
| | | MCF-7 | 52.7 | >10 |
| | | SKMES | 67.4 | >10 |

The data presented in Table I are compared to results achieved with 5-FU as the control. All compounds were dosed on an equimilimolar basis. Inhibitory concentration (IC 50) is defined as the concentration required to kill 50% of the untreated cancer cells. Although the IC 50 of certain of the compounds listed in Table I may be higher than that for 5-FU (the control), the compounds of the present invention are generally less toxic to normal cells such as bone marrow or fibroblasts. This implies that the compounds of the present invention may have advantages over known cancer therapies as the claimed compounds may be less toxic and/or more selective for the tumor cells, thereby causing less serious side effects. Additionally, because of their lower toxicity to normal cells, it is anticipated that the present compounds may be dosed at a higher rate to selectively increase toxicity to the cancer cells. In this regard, a therapeutic ratio for a given compound is typically determined by the following calculation.

$$\frac{\% \text{ survival bone marrow}}{\% \text{ survival tumor}}$$

A therapeutic ratio of <80% is considered active.

In Vivo Evaluation

Representative compounds of the present invention are being tested in a variety of preclinical tests of anti-cancer activity which are indicative of clinical utility. For example, certain compounds are being tested in vivo against human tumors xenografted into nude mice, specifically B16, MX-1 and P388 Leukemia tumor lines.

B16 Melanoma

B6D2F1 mice receive i.p. inocula of B16 murine melanoma brei prepared from B16 tumors growing s.c. in mice (day 0). On day 1, tumored mice are treated with drugs or vehicle control; the drugs, route of drug administration and schedule are selected as appropriate for the study in question. If dosing information for agents is not available, the maximum tolerated dose (MTD) is determined in initial dose finding experiments in non-tumored mice. In a typical experiment, drugs are given at their MTD and ½ MTD doses i.p. on a daily×5 schedule.

The mean survival times of all groups are calculated and results are expressed as mean survival of treated mice/mean survival of control mice (T/C)×100. A T/C value of 150 means that the treated group lived 50% longer than the control group; this is sometimes referred to as the increase in life span, or ILS value.

Mice that survive for 60 days are considered long term survivors, or cures, in the B16 model. The universally accepted cut-off for activity in this model, which has been used for years by the NCI, is T/C=125. Conventional use of B16 over the years has set the following levels of activity: T/C<125, no activity; T/C=125–150, weak activity; T/C=150–200, modest activity; T/C=200–300, high activity; T/C>300, with long term survivors' excellent, curative activity.

Statistics are performed on the data using primarily the log rank p-value test.

P388 Leukemia

This test is conducted in exactly the same way as the B16 test. The tumor inoculum is prepared by removing ascites fluid containing P388 cells from tumored DBA/2 mice, centrifuging the cells and then resuspending the leukemia cells in saline. Mice receive $1 \times 10^5$ P388 cells i.p. on day 0.

MX-1 Human Breast Tumor Xenograft

Nude mice are implanted s.c. by trocar with fragments of MX-1 mammary carcinomas harvested from s.c. growing MX-1 tumors in nude mice hosts. When tumors are approximately 5 mm×5 mm in size (usually about ten days after inoculation), the animals are pair-matched into treatment and a control groups. Each group contains 10 tumored mice, each of which is ear-tagged and followed individually throughout the experiment. The administration of drugs or vehicle begins the day the animals are pair-matched (day 1). The doses, route of drug administration and schedule are selected as appropriate for the study in question. If the MTD dose of an agent is not known, it is determined in an initial dosing experiment in non-tumored mice. In a typical experiment, drugs are given at their MTD and ½ MTD doses i.p. on a daily×5 schedule.

The experiment is usually terminated when control tumors reach a size of 2–3 g. Mice are weighed twice weekly, and tumor measurements are taken by calipers twice weekly, starting on day 1. These tumor measurements are converted to mg tumor weight by a well-known formula, and from these calculated tumor weights the termination date can be determined. Upon termination, all mice are weighed, sacrificed and their tumors excised. Tumors are weighed, and the mean tumor weight per group is calculated. In this model, the mean control tumor weight/mean treated tumor weight×100% (C/T) is subtracted from 100% to give the tumor growth inhibition (TGI) for each group.

Some drugs cause tumor shrinkage in the MX-1 model. With these agents, the final weight of a given tumor is subtracted from its own weight at the start of treatment on day 1. This difference divided by the initial tumor weight is the % shrinkage. A mean % tumor shrinkage can be calculated from data from the mice in a group that experienced MX-1 regressions. If the tumor completely disappears in a mouse, this is considered a complete regression or complete tumor shrinkage. If desired, mice with partial or total tumor regressions can be kept alive past the termination date to see whether they live to become long term, tumor-free survivors.

Statistics are performed on the data using primarily the log rank p-value test.

Protocols for HIV-1 Inactivation Studies

General protocols for the testing of compounds in in vitro antiviral screens are disclosed in the following references:

1) Perez, V. L., Rowe, T., Justement, J. S., Butera, S. T., June, C. H. and Folks, T. M., An HIV-1-infected T cell clone defective in IL-2 production and $Ca^{++}$ mobilization after CD3 stimulation, *J. Immunol.*, 147:3145–3148, 1991.

2) Folks, T. M., Justement, J., Kinter, A., Dinarello, C. and Fauci, A. S., Cytokine-induced expression of HIV-1 in a chronically infected promonocyte cell line, *Science*, 238:800–802, 1987.

3) Folks, T. M., Clouse, K. A., Justement, J., Rabson, A., Duh, E., Kehrl, J. H. and Fauci, A. S., Tumor necrosis factor α induces expression of human immunodeficiency virus in a chronically infected T-cell clone, *Proc. Natl. Acad. Sci. USA*, 86:2365–2368, 1989.

4) Clouse, K. A., Powell, D., Washington, I., Poli, G., Strebel, K., Farrar, W., Barstad, P., Kovacs, J., Fauci, A. S. and Folks, T. M., Monokine regulation of human immunodeficiency virus-1 expression in a chronically infected human T cell clone, *J. Immunol.*, 142:431–438, 1989.

1. Inactivation of Cell-free HIV-1.

Cell-free HIV-1 stocks are derived from culture supernatants of H-9 human T cells chronically infected with the HTLV-IIIB strain of HIV-1. Other HIV-1 strains including the MN and some African strains may be used later for confirmatory purposes.

a) Cell-free HTLV-IIIB:

Cell-free HIV-1 ($5 \times 10^5$ to $1 \times 10^6$ TCID$_{50}$/ml, or median tissue culture infectious dose) is either left untreated or treated with RPMI 1640 culture medium, or with different concentrations of antivirals for various time intervals at 37° C., or at a temperature to be determined. After incubation, the treated and untreated are added to $5 \times 10^5$ washed and pelleted target MT-4 cells. After 1 h incubation at 37° C., the MT-4 cells are washed three times with RPMI 1604, resuspended in RPMI 1640 supplemented with 15% fetal bovine serum (FBS) and cultured in a 5% $CO_2$ humidified incubator at 37° C. Cell viability is determined on day 7 of culture by the addition of the 3-(4,5-dimethyl-thiazol-2-yl)-2,5-diphenyitetrazolium bromide (MTT) dye, which changes in color in the presence of live mitochondria. All determinations are done in triplicates.

b) Cell-free JR-CSF:

In addition to assessing the effects of antivirals on a lab strain of HIV-1 (HTLV-IIIB), it is also important to determine antiviral effects on a primary isolate of HIV-1 (JR-CSF), which only infects primary human peripheral mononuclear cells (PBMCs). Human PBMCs activated with phytohemagglutinin A (PHA, Sigma Chemical Co.) are prepared by culturing PBMCs in RPMI 1640 culture medium supplemented with 10% FBS (complete medium) and 2.0 μg of PHA/ml for 1 day before used in infectivity studies. HIV-1 (JR-CSF) untreated or treated as above are added to PHA-activated human PBMCs and incubated for 1 h at 37° C. After incubation, 1.0 ml of complete RPMI 1640 culture medium is added to the cells. Culture supernatants are collected on days 3, 6 and 9 of culture and the amounts of HIV-1 p24 core protein are determined in triplicate by the HIV-1 p24 antigen capture assay (Coulter Immunology, FL, or NEN-DuPont, Wilmington, Del.).

2. Inactivation of Cell-associated HIV-1.

HIV-1-infected human cells to be used include the chronically infected H-9 cells (HTLV-IIIB or MN strains) and human PBMCs infected with HTLV-IIIB or with JR-CSF. HTLV-IIIB- and MN-infected H-9 cell lines are available in various laboratories. For infected human PBMCs, fresh human PBMCs are obtained from normal volunteers and stimulated with PHA, and infected with HTLV-IIIB or JR-CSF, as described above. On day 7 after in vitro infection, infectivity is checked by testing for the presence of HIV-1 p24 in the culture supernatants. Infected cultures are divided in equal aliquots. One set is then treated with antivirals at different concentrations for various time intervals, whereas one set is left untreated. Culture supernatants collected on days 3, 6 and 9 of culture will be assessed for HIV-1 p24 levels by the p24 antigen capture assay kit. Cells from these cultures can also be used in immunofluorescence (IF) studies to determine the percentage of cells expressing HIV-1 antigen(s).

3. Inactivation of HIV-1 Latently Infected Cells.

These assays are designed to study the effects of antivirals on HIV-1 latently infected cells. One or more of the following HIV-1 latently infected human cell lines can be used (J1-1, U1/HIV, and ACH-2 obtained from the NIH AIDS Research and Reagent Reference Program, Rockville, Md.). These cells are characterized by HIV-1 infection without significant HIV-1 viral replication unless they are stimulated with different cytokines which results in a 10–100 fold increase in HIV-1 replication. J1-1, or U1/HIV, or ACH-2 cells are seeded in 96-well round-bottom tissue culture plates to give $5 \times 10^5$/well in RPMI 1640 supplemented with 15% fetal bovine serum (FBS). The cells are either left untreated or treated with different concentrations of antivirals for various time intervals. Subsequent to treatment, treated and untreated cells are washed three times in RPMI 1640 and are stimulated as follows.

The J1-1 cells are stimulated with 1000 U of α tumor necrosis factor (α-TNF, Genzyme) for 48 h at 37° C., as previously described (Reference 1).

The U1/HIV-1 cells are stimulated with 20%–40% PHA-culture supernatant (Electronucleonics) for 48 h at 37° C. (Reference 2). The PHA-supernatant will either be purchased from Electronucleonics or will be prepared in our laboratory. To prepare PHA-supernatant, normal human PBMC will be cultured at a cell density of $10^6$ cells/ml in RPMI 1640 supplemented with 15% FBS and 10 μg/ml of phytohemagglutinin A (PHA, Sigma Chemical Co.). The culture supernatant will be harvested, filtered through a 2 μm filter and used to stimulate the U1/HIV cells as described above.

The ACH-2 cells will be stimulated by addition of 1.0 μM of phorbal 12-myristate 13 acetate (PMA, Sigma Chemical Co.) for 48 h at 37° C. as described (References 3 and 4). At the end of the stimulation period, culture supernatants are collected and HIV-1 expression is assessed by the HIV-1 p24 antigen capture ELISA (DuPont) and by the reverse transcriptase (RT).

In inactivation of cell-associated HIV-1 experiments, the treated and untreated cells could also be submitted to PCR analysis.

4. Inhibition of HIV-1-induced Syncytium Formation.

HIV-1-infected H-9 cells are left untreated or treated with antiviral as described above. Treated and untreated cells ($5 \times 10^4$ cells/well) are added to 96-well flat-bottom microtiter tissue culture plates containing $1 \times 10^5$ indicator SupT1 human T cells/well in complete RPMI 1640 culture medium. Following overnight incubation at 37° C., syncytium formation is scored by two independent people using an inverted microscope scope.

5. Cytotoxicity Studies.

The cytotoxicity of the antivirals can be tested on a variety of cell types. All of the cell lines used above and normal human PBMCs are incubated with different antiviral concentrations for various time intervals as described above. Cytotoxicity is determined by the MTT dye method (see above) and by [$^3$H]thymidine uptake and scintillation counting.

Dosage and Formulation

The antitumor compounds (active ingredients) of this invention can be administered to inhibit tumors by any means that produces contact of the active ingredient with the agent's site of action in the body of a mammal. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

The dosage administered will be a tumor-inhibiting amount of active ingredient and will, of course, vary depending upon known factors such as the pharmacodymanic characteristics of the particular active ingredient and its mode and route of administration; age, health and weight of the recipient; nature and extent of symptoms; kind of concurrent treatment, frequency of treatment and the effect desired. Usually a daily dosage (therapeutic effective amount or cancer-inhibiting amount) of active ingredient can be about 5 to 400 milligrams per kilogram of body weight. Ordinarily, 10 to 200, and preferably 10 to 50, milligrams per kilogram per day given in divided doses 2 to 4 times a day or in sustained release form is effective to obtain desired results.

Dosage forms (compositions) suitable for internal administration contain from about 1.0 milligram to about 500 milligrams of active ingredient per unit. In these pharmaceutical compositions, the active ingredient will ordinarily be present in an amount of about 0.05–95% by weight based on the total weight of the composition.

The active ingredient can be administered orally in solid dosage forms such as capsules, tablets and powders, or in liquid dosage forms such as elixirs, syrups and suspensions. It can also be administered parenterally, in sterile liquid dosage forms.

Gelatin capsules contain the active ingredient and powdered carriers such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents and, if necessary, buffer substances. Antioxidizing agents such as sodium bisulfate, sodium sulfite or ascorbic acid either alone or combined are suitable stabilizing agents. Also used are citric acid and its salts and sodium EDTA. In addition, parenteral solutions can contain preservatives such as benzalkonium chloride, methyl- or propyl-paraben and chlorobutanol.

Suitable pharmaceutical carriers are described in Remington's Pharmaceutical Sciences, Mack Publishing Company, a standard reference text in this field.

Useful pharmaceutical dosage forms for administration of the compounds of this invention can be illustrated as follows.

Capsules: Capsules are prepared by filling standard two-piece hard gelatin capsulates each with 100 milligrams of powdered active ingredient, 175 milligrams of lactose, 24 milligrams of talc and 6 milligrams magnesium stearate.

Soft Gelatin Capsules: A mixture of active ingredient in soybean oil is prepared and injected by means of a positive displacement pump into gelatin to form soft gelatin capsules containing 100 milligrams of the active ingredient. The capsules are then washed and dried.

Tablets: Tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of cornstarch and 98.8 milligrams of lactose. Appropriate coatings may be applied to increase palatability or to delay absorption.

Injectable: A parenteral composition suitable for administration by injection is prepared by stirring 1.5% by weight of active ingredients in 10% by volume propylene glycol and water. The solution is made isotonic with sodium chloride and sterilized.

Suspension: An aqueous suspension is prepared for oral administration so that each 5 millimeters contain 100 milligrams of finely divided active ingredient, 200 milligrams of sodium carboxymethyl cellulose, 5 milligrams of sodium benzoate, 1.0 grams of sorbitol solution U.S.P. and 0.025 millimeters of vanillin.

In the present disclosure it should be understood that the specified materials and conditions are important in practicing the invention but that unspecified materials and conditions are not excluded so long as they do not prevent the benefits of the invention from being realized.

What is claimed:

1. A compound of the formula:

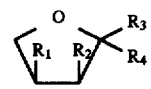

or a pharmaceutically acceptable salt thereof, wherein:

$R_1$ and $R_2$ are independently H, mono- or di-halogen, or $OR_5$ wherein $R_5$ is H, $COR_6$, $P(O)_n R_7 R_8$ wherein $R_6$ is substituted or unsubstituted alkyl of 1–5 carbon atoms or a substituted or unsubstituted aromatic ring structure, $R_7$ and $R_8$ are each H or alkyl of 1–5 carbon atoms and n is 2 or 3;

$R_3$ and $R_4$ are independently B, H or $OR_9$ where $R_9$ is H, $COR_{10}$, $P(O)_m R_{11} R_{12}$ wherein $R_{10}$ is substituted or unsubstituted alkyl of 1–5 carbon atoms or a substituted or unsubstituted aromatic ring structure and $R_{11}$ and $R_{12}$ are each H or alkyl of 1–5 carbon atoms and m is 2 or 3; and B is selected from a naturally-occurring nucleobase or a substituted nucleobase wherein said substitutions are selected from the group consisting of H, halogen, C1–C6 alkyl, C2–C6 alkenyl, C1–C6 alkoxy, C3–C6 cycloalkyl-C1–C6 alkoxy, C3–C8 cycloalkyloxy, C3–C8 cycloalkylthio, C1–C6 alkylthio, a substituted amino group, an aryl, aralkyl, aryloxy, aralkoxy, arylthio, aralkylthio, a heterocyclic ring and an amino group, provided that when the base is a pyrimidine, the atom at position 4 of the base can be sulfur and further provided that when the base is a purine, the atom at position 6 of the base may be sulfur;

provided that: only one of $R_3$ or $R_4$ can be B; when $R_4$ is B and B is 5-fluorouracil, then $R_1$ and $R_2$ cannot both be H; when $R_1$ and $R_2$ are each OH, $R_3$ is H and $R_4$ is B, then B cannot be A; and when $R_1$ and $R_2$ are each OH, $R_4$ is H and $R_3$ is B, then B cannot be A.

2. A compound of claim 1 wherein $R_3$ is defined as B and $R_4$ is H.

3. A compound of claim 1 wherein $R_4$ is defined as B and $R_3$ is H.

4. A compound of claim 1 wherein B is a nucleobase or substituted nucleobase selected from the group consisting of C, T, U, G, A, hypoxanthine and 5-fluorouracil.

5. A compound of claim 1 wherein $R_1$–$R_2$ are each OH.

6. A compound of claim 1 wherein $R_3$ is B; $R_4$ is H; B is a nucleobase selected from the group consisting of C, T, U, G, A, hypoxanthine and 5-fluorouracil; and $R_1$–$R_2$ are each OH.

7. A compound of claim 1 wherein $R_4$ is B; $R_3$ is H; B is a nucleobase selected from the group consisting of C, T, U, G, A, hypoxanthine and 5-fluorouracil; and $R_1$–$R_2$ are each OH.

8. The compound of claim 1 which is selected from the group consisting of β-L-erythrofuranosyl-5-fluorouracil; β-L-erythrofuranosyluracil; β-L-erythrofuranosylcystosine; β-L-erythrofuranosylhypoxanthine; β-L-erythrofuranosylguanine; α-L-erythrofuranosyl-5-fluorouracil; and 3'-azido-2',3'-dideoxy-β-L-erythrofuranosylthymine or a pharmaceutically acceptable salts thereof.

9. A pharmaceutical composition comprising a pharmaceutically acceptable carrier and a therapeutically effective amount of one or more of the compounds of claim 1.

10. A pharmaceutical composition comprising a pharmaceutically acceptable carrier and a therapeutically effective amount of one or more of the compounds of claim 8.

11. A method of treating cancer in a mammal, the method comprising administering to a mammal bearing a cancer, a cancer-inhibiting amount of a compound of claim 8.

* * * * *